(12) United States Patent
Araki et al.

(10) Patent No.: US 10,016,749 B2
(45) Date of Patent: Jul. 10, 2018

(54) CATALYST COMPOSITION FOR HYDROGENATION AND METHOD FOR HYDROGENATION USING THE SAME

(71) Applicant: Asahi Kasei Chemicals Corporation, Tokyo (JP)

(72) Inventors: Yoshifumi Araki, Tokyo (JP); Eiji Sasaya, Tokyo (JP); Katsunori Nitta, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 0 days.

(21) Appl. No.: 14/428,622

(22) PCT Filed: Sep. 12, 2013

(86) PCT No.: PCT/JP2013/074749
§ 371 (c)(1),
(2) Date: Mar. 16, 2015

(87) PCT Pub. No.: WO2014/046017
PCT Pub. Date: Mar. 27, 2014

(65) Prior Publication Data
US 2015/0273459 A1    Oct. 1, 2015

(30) Foreign Application Priority Data

Sep. 21, 2012    (JP) .............................. 2012-208283

(51) Int. Cl.
| | | |
|---|---|---|
| C08C 19/02 | (2006.01) | |
| B01J 31/22 | (2006.01) | |
| B01J 31/02 | (2006.01) | |
| B01J 31/12 | (2006.01) | |
| B01J 31/14 | (2006.01) | |
| C07F 7/28 | (2006.01) | |
| C08F 299/02 | (2006.01) | |
| C07F 17/00 | (2006.01) | |
| C08F 8/04 | (2006.01) | |

(52) U.S. Cl.
CPC ....... B01J 31/2295 (2013.01); B01J 31/0204 (2013.01); B01J 31/0209 (2013.01); B01J 31/0237 (2013.01); B01J 31/122 (2013.01); B01J 31/143 (2013.01); B01J 31/22 (2013.01); C07F 7/28 (2013.01); C07F 17/00 (2013.01); C08C 19/02 (2013.01); C08F 8/04 (2013.01); C08F 299/02 (2013.01); B01J 2231/60 (2013.01); B01J 2231/64 (2013.01); B01J 2531/46 (2013.01)

(58) Field of Classification Search
None
See application file for complete search history.

(56) References Cited

U.S. PATENT DOCUMENTS

| | | | |
|---|---|---|---|
| 4,980,421 A | 12/1990 | Teramoto et al. | |
| 5,886,108 A * | 3/1999 | Miyamoto ................ | C08F 8/04 525/332.8 |
| 2002/0107423 A1 | 8/2002 | Miyamoto et al. | |
| 2003/0073571 A1 | 4/2003 | Van Der Heijden et al. | |
| 2008/0146733 A1 | 6/2008 | Tsai et al. | |
| 2010/0036068 A1 | 2/2010 | Aso et al. | |

FOREIGN PATENT DOCUMENTS

| | | |
|---|---|---|
| JP | 61028507 A | 2/1986 |
| JP | 61033132 A | 2/1986 |

(Continued)

OTHER PUBLICATIONS

Computer Translation of JP 08-33846 (1996).*

(Continued)

Primary Examiner — Robert C Boyle
(74) Attorney, Agent, or Firm — Morgan, Lewis & Bockius LLP

(57) ABSTRACT

A catalyst composition for hydrogenation including (A) to (D), in which a mass ratio ((C)/(A)) is 0.1 to 4.0 and a mass ratio ((D)/(A)) is 0.01 to 1.00,
(A): a titanocene compound represented by formula (1),

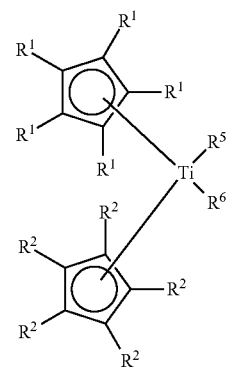
(1)

(wherein $R^5$ and $R^6$ are any group selected from hydrogen, a hydrocarbon group having 1 to 12 carbon atoms, an aryloxy group, an alkoxy group, a halogen group, and a carbonyl group. $R^1$ and $R^2$ are any group selected from the group consisting of hydrogen and a hydrocarbon group having 1 to 12 carbon atoms, and $R^1$ and $R^2$ are not all hydrogen atoms or all a hydrocarbon group having 1 to 12 carbon atoms),
(B): a reductant formed from a compound containing an element selected from the elements Li, Na, K, Mg, Zn, Al, and Ca,
(C): an unsaturated compound having a molecular weight of 400 or less, and
(D): a polar compound.

25 Claims, No Drawings

(56) References Cited

FOREIGN PATENT DOCUMENTS

| | | | |
|---|---|---|---|
| JP | 61047706 A | 3/1986 | |
| JP | 62209103 A | 9/1987 | |
| JP | 63005402 A | 1/1988 | |
| JP | 01053851 A | 3/1989 | |
| JP | 01275605 A | 11/1989 | |
| JP | 02172537 A | 7/1990 | |
| JP | 04096904 A | 3/1992 | |
| JP | 08027216 A | 1/1996 | |
| JP | 08-33846 | * | 2/1996 |
| JP | 08033846 A | 2/1996 | |
| JP | 08041081 A | 2/1996 | |
| JP | 2003524515 A | 8/2003 | |
| JP | 2004/269665 | * | 9/2004 |
| JP | 2004269665 A | 9/2004 | |
| JP | 2010059415 A | 3/2010 | |
| TW | 2012-26054 | 7/2012 | |
| WO | 2002002650 A1 | 1/2002 | |

OTHER PUBLICATIONS

Computer Translation of JP 2004-269665 (2004).*
European Search Report issued in related European Patent Application No. 13839238.6 dated Aug. 5, 2015.
International Search Report issued in corresponding International Patent Application No. PCT/JP2013/074749 dated Oct. 8, 2013.
Yin-Heng Fan et al., Extremely active catalysts for the hydrogenation of terminal alkenes, Journal of Catalysis, published online Jan. 3, 2002, vol. 205, pp. 294-298.
Kubik, Stefan, ed., "Unsaturated," XP055321514, https://roempp.thieme.de/roempp4.0/do/data/RD-21-00497 (Nov. 30, 2005).

* cited by examiner

CATALYST COMPOSITION FOR HYDROGENATION AND METHOD FOR HYDROGENATION USING THE SAME

TECHNICAL FIELD

The present invention relates to a catalyst composition for hydrogenation and a method for selectively hydrogenating (hereinafter sometimes simply referred to as "hydrogenation") an olefinic unsaturated double bond-containing compound (hereinafter sometimes simply referred to as olefinic compound) using this catalyst composition for hydrogenation.

BACKGROUND ART

Conventionally, generally, catalysts of a heterogeneous system and catalysts of a homogenous system are known as a catalyst for hydrogenation to be used in the step of hydrogenating an olefinic compound.

Although the former catalysts of the heterogeneous system are widely used industrially, the catalysts of the heterogeneous system generally have lower activity than that of the latter catalysts of the homogenous system and have the problem of being economically inefficient, because the catalysts of the heterogeneous system are required to be used at a large amount for a desired hydrogenation reaction, and the reaction is at a high temperature and a high pressure.

On the other hand, since a hydrogenation reaction using the latter catalysts of the homogenous system usually proceeds in the homogenous system, there are features that the catalysts of the homogenous system have a higher activity, require a lower amount of used catalyst, and are capable of hydrogenation at a lower temperature and a lower pressure as compared with the catalysts of the heterogeneous system. However, the catalysts of the homogenous system have the drawbacks that catalyst preparation is complex, the stability of the catalyst itself cannot be said to be sufficient, reproducibilities are poor, and side reactions tend to occur. Further, the catalysts of the homogenous system also have the problem that sufficient activity of hydrogenation is not obtained when hydrogenating an alkyl-substituted olefinic unsaturated double bond having a steric hindrance.

In view of the above, there is currently a strong need for the development of a catalyst for hydrogenation which has a high activity and which can be handled easily.

In addition, for a polymer containing an olefinic unsaturated double bond, although the unsaturated double bond is advantageously utilized in vulcanization and the like, due to this double bond, the polymer also has the drawbacks regarding poor stability, such as heat resistance and oxidation resistance. This drawback regarding poor stability is substantially improved by hydrogenating the polymer to remove the unsaturated double bonds in the polymer chain.

However, when hydrogenating the polymer, as compared with hydrogenating a low-molecular-weight compound, the polymer is more easily affected by the viscosity of the reaction system, steric hindrance of the polymer chain and the like, which makes hydrogenation more difficult. In addition, there is the drawback that it is very difficult to physically remove the catalyst and substantially impossible to completely separate the catalyst, after hydrogenation has finished.

As described above, there has long been an issue for obtaining a catalyst for hydrogenation that is economically efficient not need to be used in a large amount, has a high storage stability, can exhibit sufficient hydrogenation activity even when hydrogenating olefinic unsaturated double bonds having a steric hindrance, and can be easily separated and removed after hydrogenation.

In consideration of such an issue, Patent Literature 1 and 2 disclose a method for hydrogenating an olefin compound using a combination of a specific titanocene compound and alkyl lithium. Patent Literature 3 and 4 disclose a method for hydrogenating an olefinic unsaturated (co)polymer using a combination of a metallocene compound and organic aluminum, zinc, and magnesium. Patent Literature 5 and 6 disclose a method for hydrogenating an olefinic unsaturated group-containing living polymer using a combination of a specific titanocene compound and alkyl lithium.

Further, Patent Literature 7 discloses a method for hydrogenating the olefinic double bond in an olefinic unsaturated double bond group-containing polymer using a combination of a specific titanocene compound and alkoxy lithium. It is noted that this method also requires an expensive organic metal compound in addition to the alkoxy lithium as a reductant.

In addition, Patent Literature 8 discloses a method for hydrogenating an olefinic unsaturated double bond containing polymer using a combination of a specific titanocene compound, an olefin compound, and a reductant.

Still further, Patent Literature 9 discloses a method for hydrogenating an olefin compound using a combination of a metallocene compound having a pentamethylcyclopentadienyl group in which all five hydrogen atoms of a cyclopentadienyl group have been substituted on with a methyl group, and a reducing agent.

Still even further, Patent Literature 10 and 11 disclose a method for hydrogenating an olefin compound using a catalyst composition for hydrogenation which includes a specific titanocene compound, a reductant, an olefinic unsaturated double bond-containing polymer, and a polar compound.

Further, Patent Literature 12 discloses a method for hydrogenating an olefin compound using a catalyst composition for hydrogenation which includes a specific metallocene compound and a compound selected from a conjugated diene monomer, an acetylene compound, and an acetylene monomer.

CITATION LIST

Patent Literature

Patent Literature 1: Japanese Patent Laid-Open No. 61-33132
Patent Literature 2: Japanese Patent Laid-Open No. 1-53851
Patent Literature 3: Japanese Patent Laid-Open No. 61-28507
Patent Literature 4: Japanese Patent Laid-Open No. 62-209103
Patent Literature 5: Japanese Patent Laid-Open No. 61-47706
Patent Literature 6: Japanese Patent Laid-Open No. 63-5402
Patent Literature 7: Japanese Patent Laid-Open No. 1-275605
Patent Literature 8: Japanese Patent Laid-Open No. 2-172537
Patent Literature 9: Japanese Patent Laid-Open No. 4-96904
Patent Literature 10: Japanese Patent Laid-Open No. 08-33846
Patent Literature 11: Japanese Patent Laid-Open No. 08-41081

Patent Literature 12: Japanese Patent Laid-Open No. 2004-269665

SUMMARY of INVENTION

Technical Problem

However, none the above-described conventionally-proposed techniques yet have sufficient properties as a catalyst for hydrogenation.

Accordingly, it is an object of the present invention to provide a catalyst composition for hydrogenation which is capable of hydrogenating an olefinic unsaturated double bond-containing compound (including a polymer containing an olefinic unsaturated double bond) with an economical advantage, which has excellent storage stability and good feed properties, and which is capable of producing a polymer having excellent non-coloration properties in a step of hydrogenation.

Solution to Problem

As a result of intensive studies to solve the problems in the above-described conventional art, the present inventors have found that the problems in the above-described conventional art could be solved by, in a catalyst composition for hydrogenation comprising a predetermined titanocene compound (A), a compound containing a predetermined element (B), a predetermined unsaturated polymer (C), and a predetermined polar compound (D), specifying the range of a mass ratio of the component (C) to the component (A) ((C)/(A)) and the range of a mass ratio of the component (D) to the component (A) ((D)/(A)), thereby completing the present invention.

Namely, the present invention is as follows.

[1]

A catalyst composition for hydrogenation comprising components (A), (B), (C), and (D) shown below,
wherein a mass ratio of the (C) to the (A) ((C)/(A)) is in a range of 0.1 to 4.0, and
wherein a mass ratio of the (D) to the (A) ((D)/(A)) is in a range of 0.01 to 1.00,
(A): a titanocene compound represented by following general formula (1),

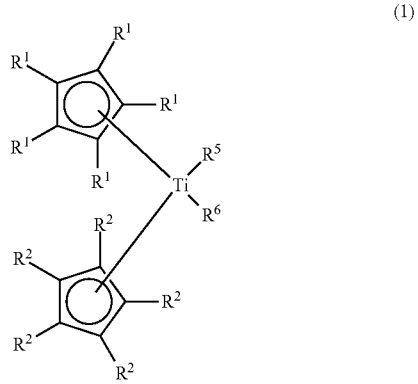

(1)

wherein $R^5$ and $R^6$ represent any group selected from the group consisting of hydrogen, a hydrocarbon group having 1 to 12 carbon atoms, an aryloxy group, an alkoxy group, a halogen group, and a carbonyl group, and $R^5$ and $R^6$ may be the same or different. $R^1$ and $R^2$ represent any group selected from the group consisting of hydrogen and a hydrocarbon group having 1 to 12 carbon atoms, and $R^1$ and $R^2$ may be the same or different, provided that $R^1$ and $R^2$ are not all hydrogen atoms or all a hydrocarbon group having 1 to 12 carbon atoms.

(B): a compound containing one or more elements selected from the group consisting of elements Li, Na, K, Mg, Zn, Al, and Ca, (C): an unsaturated polymer having a molecular weight of 400 or less, and (D): a polar compound.

[2]

The catalyst composition for hydrogenation according to [1] above, wherein the (C) has an unsaturated group content of 2 mol or more based on 1 mol of the (C).

[3]

The catalyst composition for hydrogenation according to [1] or [2] above, wherein the (B) is an organic lithium compound.

[4]

A method for hydrogenation, comprising bringing an olefinic unsaturated double bond-containing compound into contact with hydrogen in an inert organic solvent, in the presence of the catalyst composition according to any one of [1] to [3] above.

[5]

The method for hydrogenation according to [4] above, wherein the olefinic unsaturated double bond-containing compound is a conjugated diene polymer or a copolymer formed of a conjugated diene and a vinyl aromatic hydrocarbon.

Advantageous Effects of Invention

According to the present invention, a catalyst composition for hydrogenation can be provided which has a high activity of hydrogenation, good feed properties, and excellent storage stability, and which is capable of producing a hydrogenated olefinic compound having excellent non-coloration properties.

DESCRIPTION OF EMBODIMENT

An embodiment for carrying out the present invention (hereinafter referred to as "present embodiment") will be described in detail below.

The present embodiment described below is an example for describing the present invention. The present invention is not limited to the following content, and may be appropriately modified within the scope thereof.

[Catalyst Composition for Hydrogenation]

The catalyst composition for hydrogenation according to the present embodiment includes the below-described (A), (B), (C), and (D), in which a mass ratio of the (C) below to the (A) below ((C)/(A)) is in a range of 0.1 to 4.0 and a mass ratio of the (D) below to the (A) below ((D)/(A)) is in a range of 0.01 to 1.00.

(Components Constituting the Catalyst Composition for Hydrogenation)

The components constituting the catalyst composition for hydrogenation according to the present embodiment are described below in detail.

Component (A): A Titanocene Compound

Component (A): a titanocene compound (in the present specification, sometimes simply referred to as component (A) or (A)) is represented by following general formula (1).

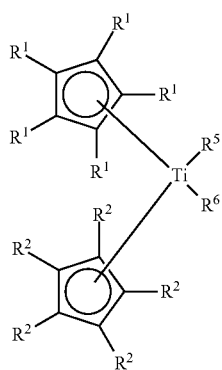

(1)

In formula (1), $R^5$ and $R^6$ represent any group selected from the group consisting of hydrogen, a hydrocarbon group having 1 to 12 carbon atoms, an aryloxy group, an alkoxy group, a halogen group, and a carbonyl group, and $R^5$ and $R^6$ may be the same or different.

$R^1$ and $R^2$ represent any group selected from the group consisting of hydrogen and a hydrocarbon group having 1 to 12 carbon atoms, and $R^1$ and $R^2$ may be the same or different, provided that $R^1$ and $R^2$ are not all hydrogen atoms or all a hydrocarbon group having 1 to 12 carbon atoms.

Examples of the hydrocarbon group having 1 to 12 carbon atoms of $R^1$, $R^2$, $R^5$, and $R^6$ in general formula (1) also include substituents represented by following general formula (2).

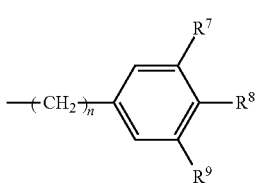

(2)

Note that $R^7$ to $R^9$ represent hydrogen or an alkyl hydrocarbon group having 1 to 4 carbon atoms, and at least any of $R^7$ to $R^9$ is hydrogen, and n=0 or 1.

Examples of component (A): a titanocene compound include, but are not limited to, bis(η(5)-methylcyclopentadienyl)titanium dihydride, bis(η(5)-1,3-dimethylcyclopentadienyl)titanium dihydride, bis(η(5)-ethylcyclopentadienyl)titanium dihydride, bis(η(5)-propylcyclopentadienyl) titanium dihydride, bis(η(5)-n-butylcyclopentadienyl) titanium dihydride, bis(η(5)-methylcyclopentadienyl) titanium dimethyl, bis(η(5)-1,3-dimethylcyclopentadienyl) titanium dimethyl, bis(η(5)-ethylcyclopentadienyl)titanium dimethyl, bis(η(5)-propylcyclopentadienyl)titanium dimethyl, bis(η(5)-n-butylcyclopentadienyl)titanium dimethyl, bis(η(5)-methylcyclopentadienyl)titanium diethyl, bis(η(5)-1,3-dimethylcyclopentadienyl)titanium diethyl, bis(η(5)-ethylcyclopentadienyl)titanium diethyl, bis(η(5)-propylcyclopentadienyl)titanium diethyl, bis(η(5)-n-butylcyclopentadienyl)titanium diethyl, bis(η(5)-methylcyclopentadienyl)titanium di-sec-butyl, bis(η(5)-1,3-dimethylcyclopentadienyl)titanium di-sec-butyl, bis(η(5)-ethylcyclopentadienyl)titanium di-sec-butyl, bis(η(5)-propylcyclopentadienyl)titanium di-sec-butyl, bis(η(5)-n-butylcyclopentadienyl)titanium di-sec-butyl, bis(η(5)-methylcyclopentadienyl)titanium dihexyl, bis(η(5)-1,3-dimethylcyclopentadienyl)titanium dihexyl, bis(η(5)-ethylcyclopentadienyl)titanium dihexyl, bis(η(5)-propylcyclopentadienyl)titanium dihexyl, bis(η(5)-n-butylcyclopentadienyl)titanium dihexyl, bis(η(5)-methylcyclopentadienyl)titanium dioctyl, bis(η(5)-1,3-dimethylcyclopentadienyl)titanium dioctyl, bis(η(5)-ethylcyclopentadienyl)titanium dioctyl, bis(η(5)-propylcyclopentadienyl)titanium dioctyl, bis(η(5)-n-butylcyclopentadienyl)titanium dioctyl, bis(η(5)-methylcyclopentadienyl)titanium dimethoxide, bis(η(5)-1,3-dimethylcyclopentadienyl)titanium dimethoxide, bis(η(5)-ethylcyclopentadienyl)titanium dimethoxide, bis(η(5)-propylcyclopentadienyl)titanium dimethoxide, bis(η(5)-n-butylcyclopentadienyl)titanium dimethoxide, bis(η(5)-methylcyclopentadienyl)titanium diethoxide, bis(η(5)-1,3-dimethylcyclopentadienyl)titanium diethoxide, bis(η(5)-ethylcyclopentadienyl)titanium diethoxide, bis(η(5)-propylcyclopentadienyl)titanium diethoxide, bis(η(5)-n-butylcyclopentadienyl)titanium diethoxide, bis(η(5)-methylcyclopentadienyl)titanium dipropoxide, bis(η(5)-dimethylcyclopentadienyl)titanium dipropoxide, bis(η(5)-ethylcyclopentadienyl)titanium dipropoxide, bis(η(5)-propylcyclopentadienyl)titanium dipropoxide, bis(η(5)-n-butylcyclopentadienyl)titanium dipropoxide, bis(η(5)-methylcyclopentadienyl)titanium dibutoxide, bis(η(5)-1,3-dimethylcyclopentadienyl)titanium dibutoxide, bis(η(5)-ethylcyclopentadienyl)titanium dibutoxide, bis(η(5)-propylcyclopentadienyl)titanium dibutoxide, bis(η(5)-n-butylcyclopentadienyl)titanium dibutoxide, bis(η(5)-methylcyclopentadienyl)titanium diphenyl, bis(η(5)-1,3-methylcyclopentadienyl)titanium diphenyl, bis(η(5)-ethylcyclopentadienyl)titanium diphenyl, bis(η(5)-propylcyclopentadienyl)titanium diphenyl, bis(η(5)-n-butylcyclopentadienyl)titanium diphenyl, bis(η(5)-methylcyclopentadienyl)titanium di(m-tolyl), bis(η(5)-1,3-methylcyclopentadienyl)titanium di(m-tolyl), bis(η(5)-ethylcyclopentadienyl)titanium di(m-tolyl), bis(η(5)-propylcyclopentadienyl)titanium di(m-tolyl), bis(η(5)-n-butylcyclopentadienyl)titanium di(m-tolyl), bis(η(5)-methylcyclopentadienyl)titanium di(p-tolyl), bis(η(5)-1,3-methylcyclopentadienyl)titanium di(p-tolyl), bis(η(5)-ethylcyclopentadienyl)titanium di(p-tolyl), bis(η(5)-propylcyclopentadienyl)titanium di(p-tolyl), bis(η(5)-n-butylcyclopentadienyl)titanium di(p-tolyl), bis(η(5)-methylcyclopentadienyl)titanium di(m,p-xylyl), bis(η(5)-1,3-dimethylcyclopentadienyl)titanium di(m,p-xylyl), bis(η(5)-ethylcyclopentadienyl)titanium di(m,p-xylyl), bis(η(5)-propylcyclopentadienyl)titanium di(m,p-xylyl), bis(η(5)-n-butylcyclopentadienyl)titanium di(m,p-xylyl), bis(η(5)-methylcyclopentadienyl)titanium di(4-ethyl phenyl), bis(η(5)-1,3-dimethylcyclopentadienyl)titanium di(4-ethyl phenyl), bis(η(5)-ethylcyclopentadienyl)titanium di(4-ethyl phenyl), bis(η(5)-propylcyclopentadienyl)titanium di(4-ethyl phenyl), bis(η(5)-n-butylcyclopentadienyl)titanium di(4-ethyl phenyl), bis(η(5)-methylcyclopentadienyl)titanium di(4-hexyl phenyl), bis(η(5)-1,3-dimethylcyclopentadienyl)titanium di(4-hexyl phenyl), bis(η(5)-ethylcyclopentadienyl)titanium di(4-hexyl phenyl), bis(η(5)-propylcyclopentadienyl)titanium di(4-hexyl phenyl), bis(η(5)-n-butylcyclopentadienyl)titanium di(4-hexyl phenyl), bis(η(5)-methylcyclopentadienyl)titanium diphenoxide, bis(η(5)-1,3-dimethylcyclopentadienyl)titanium diphenoxide, bis(η(5)-ethylcyclopentadienyl)titanium diphenoxide, bis(η(5)-propylcyclopentadienyl)titanium diphenoxide, bis(η(5)-n-butylcyclopentadienyl)titanium diphenoxide, bis(η(5)-n-butylcyclopentadienyl)titanium di(4-hexyl phenyl), bis(η(5)-methylcyclopentadienyl)titanium difluoride, bis(η(5)-1, 3-dimethylcyclopentadienyl)titanium difluoride, bis(η(5)-ethylcyclopentadienyl)titanium difluoride, bis(η(5)-propylcyclopentadienyl)titanium difluoride, bis(η(5)-n-butylcyclopentadienyl)titanium difluoride, bis(η(5)-methylcyclopentadienyl)titanium dichloride, bis(η(5)-1,3-dimethylcyclopentadienyl)titanium dichloride, bis(η(5)-ethylcyclopentadienyl)titanium dichloride, bis(η(5)-propylcyclopentadienyl)titanium dichloride, bis(η(5)-n-butylcyclopentadienyl)titanium dichloride, bis(η(5)-methylcyclopentadienyl)titanium dibromide, bis(η(5)-1,3-dimethylcyclopentadienyl)titanium dibromide, bis(η(5)-ethylcyclopentadienyl)titanium dibromide, bis(η(5)-propylcyclopentadienyl)titanium dibromide, bis(η(5)-n-butylcyclopentadienyl)titanium dibromide, bis(η(5)-methylcyclopentadienyl)titanium diiodide, bis(η(5)-1,3-dimethylcyclopentadienyl)titanium diiodide, bis(η(5)-ethylcyclopentadienyl)titanium diiodide, bis(η(5)-propylcyclopentadienyl)titanium diiodide, bis(η(5)-n-butylcyclopentadienyl)titanium diiodide, bis(η(5)-methylcyclopentadienyl)titanium chloride methyl, bis(η(5)-di-1,3-methylcyclopentadienyl)titanium chloride methyl, bis(η(5)-ethylcyclopentadienyl)titanium chloride methyl, bis(η(5)-propylcyclopentadienyl)titanium chloride methyl, bis(η(5)-n-butylcyclopentadienyl)titanium chloride methyl, bis(η(5)-methylcyclopentadienyl)titanium chloride ethoxide, bis(η(5)-1,3-dimethylcyclopentadienyl)titanium chloride ethoxide, bis(η(5)-ethylcyclopentadienyl)titanium chloride ethoxide, bis(η(5)-propylcyclopentadienyl)titanium chloride ethoxide, bis(η(5)-n-butylcyclopentadienyl) titanium chloride ethoxide, bis(η(5)-methylcyclopentadienyl) titanium chloride phenoxaide, bis(η(5)-1,3-dimethylcyclopentadienyl)titanium chloride phenoxaide, bis(η(5)-ethylcyclopentadienyl)titanium chloride phenoxaide, bis(η(5)-propylcyclopentadienyl)titanium chloride phenoxaide, bis(η(5)-n-butylcyclopentadienyl)titanium chloride phenoxaide, bis(η(5)-methylcyclopentadienyl)titanium dibenzyl, bis(η(5)-1,3-dimethylcyclopentadienyl)titanium dibenzyl, bis(η(5)-ethylcyclopentadienyl)titanium dibenzyl, bis(η(5)-propylcyclopentadienyl)titanium dibenzyl, bis(η(5)-n-butylcyclopentadienyl)titanium dibenzyl, bis(η(5)-methylcyclopentadienyl)titanium dicarbonyl, bis(η(5)-1,3-dimethylcyclopentadienyl)titanium dicarbonyl, bis(η(5)-ethylcyclopentadienyl)titanium dicarbonyl, bis(η(5)-propylcyclopentadienyl)titanium dicarbonyl, bis(η(5)-n-butylcyclopentadienyl)titanium dicarbonyl and the like.

These may be used alone as one kind, or in combination of two kinds or more.

The titanocene compound having these alkyl group-substituted cyclopentadienyl groups is not limited to the above-described examples. Titanocene compounds other than those described above having two, three, or four alkyl group substituents on the cyclopentadienyl ring may also be preferably used.

By using the above-described various titanocene compounds, the catalyst composition for hydrogenation according to the present embodiment hydrogenates the olefinic unsaturated double bonds of the olefinic compound (olefinic unsaturated double bond-containing compound, hereinafter sometimes simply referred to as olefinic compound) in high activity, and the hydrogenated olefinic compound has excellent heat resistance. Especially, to obtain a catalyst composition for hydrogenation that has a high activity of hydrogenating the olefinic unsaturated double bonds of a conjugated diene polymer or a copolymer formed of a conjugated diene and a vinyl aromatic hydrocarbon, and hydrogenates the unsaturated double bonds in a wide temperature range, in a high activity and selectivity, the following compounds are preferred. Preferred examples of the titanocene compounds include, bis(η(5)-methylcyclopentadienyl)titanium dichloride, bis(η(5)-ethylcyclopentadienyl) titanium dichloride, bis(η(5)-propylcyclopentadienyl)titanium dichloride, bis(η(5)-n-butylcyclopentadienyl)titanium dichloride, bis(η(5)-methylcyclopentadienyl)titanium dimethyl, bis(η(5)-ethylcyclopentadienyl)titanium dimethyl, bis(η(5)-propylcyclopentadienyl)titanium dimethyl, bis(η(5)-n-butylcyclopentadienyl)titanium dimethyl, bis(η(5)-methylcyclopentadienyl)titanium di(p-tolyl), bis(η(5)-ethylcyclopentadienyl)titanium di(p-tolyl), bis(η(5)-propylcyclopentadienyl)titanium di(p-tolyl), bis(η(5)-n-butylcyclopentadienyl)titanium di(p-tolyl), bis(η(5)-methylcyclopentadienyl)titanium diphenyl, bis(η(5)-ethylcyclopentadienyl)titanium diphenyl, bis(η(5)-propylcyclopentadienyl)titanium diphenyl, bis(η(5)-n-butylcyclopentadienyl)titanium diphenyl and the like.

In addition, from the perspective of stable handling in air, preferred examples of the (A), a titanocene compound include, but are not limited to, bis(η(5)-methylcyclopentadienyl)titanium dichloride, bis(η(5)-n-butylcyclopentadienyl)titanium dichloride, bis(η(5)-methylcyclopentadienyl) titanium diphenyl, bis(η(5)-n-butylcyclopentadienyl) titanium diphenyl, bis(η(5)-methylcyclopentadienyl) titanium di(p-tolyl), and bis(η(5)-n-butylcyclopentadienyl) titanium di(p-tolyl).

The above-described component (A): a titanocene compound can be synthesized by, for example, reacting a tetravalent titanocene halogen compound having a cyclopentadienyl group that has an alkyl substituent with an aryl lithium. The structure of the synthesized titanocene compound can be identified using 1H-NMR and MS spectra.

<Component (B): A Compound Containing a Predetermined Element>

As the compound (B) containing a predetermined element (in the present specification, sometimes simply referred to as component (B) or (B)), it is used that a compound includes one or more elements selected from the group consisting of elements Li, Na, K, Mg, Zn, Al, and Ca among known organic metal compounds and metal-containing compounds having the ability of reducing the above-described component (A), a titanocene compound.

Examples of component (B): a compound containing a predetermined element include organic lithium compounds, organic sodium compounds, organic potassium compounds, organic zinc compounds, organic magnesium compounds, organic aluminum compounds, organic calcium compounds and the like. These may be used alone as one kind, or in combination of two kinds or more.

Examples of the organic lithium compounds as component (B) include, but are not limited to, methyllithium, ethyllithium, n-propyllithium, isopropyllithium, n-butyllithium, sec-butyllithium, isobutyllithium, t-butyllithium, n-pentyllithium, n-hexyllithium, phenyllithium, cyclopentadienyllithium, m-tolyllithium, p-tolyllithium, xylyllithium, dimethylaminolithium, diethylaminolithium, methoxylithium, ethoxylithium, n-propoxylithium, isopropoxylithium, n-butoxylithium, sec-butoxylithium, t-butoxylithium, pentyloxylithium, hexyloxylithium, heptyloxylithium, octyloxylithium, phenoxylithium, 4-methyl phenoxylithium, benzyloxylithium, 4-methyl benzyloxylithium and the like.

Further, a lithium phenolate compound obtained by reacting a phenol-based stabilizer with the above-described various alkyl lithiums can also be used as component (B).

Examples of such a phenol-based stabilizer include, but are not limited to, 1-oxy-3-methyl-4-isopropyl benzene, 2,6-di-t-butylphenol, 2,6-di-t-butyl-4-ethylphenol, 2,6-di-t-butyl-p-cresol, 2,6-di-t-butyl-4-n-butylphenol, 4-hydroxymethyl-2,6-di-t-butylphenol, butyl hydroxyanisole, 2-(1-methylcyclohexyl)-4,6-dimethylphenol, 2,4-dimethyl-6-t-butylphenol, 2-methyl-4,6-dinonylphenol, 2,6-di-t-butyl-α-dimethyl amino-p-cresol, methylene-bis-(dimethyl-4,6-phenol), 2,2'-methylene-bis-(4-methyl-6-t-butylphenol), 2,2'-methylene-bis-(4-methyl-6-cyclohexylphenol), 2,2'-methylene-bis-(4-ethyl-6-t-butylphenol), 4,4'-methylene-bis-(2,6-di-t-butylphenol), 2,2'-methylene-bis-(6-α-methyl-benzyl-p-cresol) and the like.

Among the above-described specific examples, it is especially preferred to use the most versatile 2,6-di-t-butyl-4-methylphenoxy lithium, which has the hydroxyl group of 2,6-di-t-butyl-p-cresol as —OLi.

Further, examples of the organic lithium compound used as component (B) include, in addition to those described above, organosilicon lithium compounds, such as trimethylsilyl lithium, diethylmethylsilyl lithium, dimethylethylsilyl lithium, triethylsilyl lithium, and triphenylsilyl lithium.

Examples of the organic sodium compound used as component (B) include, but are not limited to, methyl sodium, ethyl sodium, n-propyl sodium, isopropyl sodium, n-butyl sodium, sec-butyl sodium, isobutyl sodium, t-butyl sodium, n-pentyl sodium, n-hexyl sodium, phenyl sodium, cyclopentadienyl sodium, m-tolyl sodium, p-tolyl sodium, xylyl sodium, sodium naphthalene and the like.

Examples of the organic potassium compound used as component (B) include, but are not limited to, methyl potassium, ethyl potassium, n-propyl potassium, isopropyl potassium, n-butyl potassium, sec-butyl potassium, isobutyl potassium, t-butyl potassium, n-pentyl potassium, n-hexyl potassium, triphenylmethyl potassium, phenyl potassium, phenylethyl potassium, cyclopentadienyl potassium, m-tolyl potassium, p-tolyl potassium, xylyl potassium, potassium naphthalene and the like.

Although some of the above-described organic alkali metal compounds and the organic alkali earth metal compounds as component (B) may also be used as a living anionic polymerization initiator of a conjugated diene compound and/or a vinyl aromatic hydrocarbon compound, when the olefin compound, which is the target to be hydrogenated, is a conjugated diene polymer having the active end of these metals or is a copolymer formed of the conjugated diene and a vinyl aromatic hydrocarbon (living polymer), these active ends may also act as component (B).

Examples of the organic zinc compound as component (B) include, but are not limited to, diethylzinc, bis(η(5)-cyclopentadienyl)zinc, diphenylzinc and the like.

Examples of the organic magnesium compound as component (B) include, but are not limited to, dimethyl magnesium, diethyl magnesium, dibutyl magnesium, ethyl butyl magnesium, methyl magnesium bromide, ethyl magnesium chloride, ethyl magnesium bromide, ethyl magnesium chloride, phenyl magnesium bromide, phenyl magnesium chloride, t-butyl magnesium chloride, t-butyl magnesium bromide and the like.

Examples of the organic aluminum compound as component (B) include, but are not limited to, trimethyl aluminum, triethyl aluminum, tri-isobutyl aluminum, triphenyl aluminum, diethyl aluminum chloride, dimethyl aluminum chloride, ethyl aluminum dichloride, methyl aluminum sesquichloride, ethyl aluminum sesquichloride, diethyl aluminum hydride, di-isobutyl aluminum hydride, triphenyl aluminum, tri(2-ethylhexyl)aluminum, (2-ethylhexyl)aluminum dichloride, methylaluminoxane, ethylaluminoxane and the like.

In addition to these, further examples of component (B) include alkali (earth) metal hydrides, such as lithium hydride, potassium hydride, sodium hydride, and calcium hydride, and hydrides containing two or more kinds of metal, such as sodium aluminum hydride, potassium aluminum hydride, diisobutyl sodium aluminum hydride, tri(t-butoxy)aluminum hydride, triethyl sodium aluminum hydride, diisobutyl sodium aluminum hydride, triethyl sodium aluminum hydride, triethoxy sodium aluminum hydride, and triethyl lithium aluminum hydride.

Further, complexes synthesized by reacting in advance the above-described organic alkali metal compound with the organic aluminum compound, and complexes (ate complexes) synthesized by reacting in advance the organic alkali metal compound with the organic magnesium compound may also be used as component (B).

Note that, from the perspective of a high activity of hydrogenation, it is preferred that the organic metal compound and metal-containing compound, which are compounds containing the predetermined element (B), are Li- or Al-containing compounds. From the perspective of further higher activity of hydrogenation, it is more preferred that the organic metal compound and metal-containing compound are organic lithium compounds.

<Component (C): An Unsaturated Compound>

The (C) an unsaturated compound (in the present specification, sometimes referred to simply as component (C) or (C)) is a compound having one or more unsaturated groups in a molecule and having a molecular weight of 400 or less.

From the perspective of the feed properties after storage of the catalyst composition for hydrogenation, the molecular weight of component (C) is 400 or less, preferably 300 or less, more preferably 200 or less, and even more preferably 150 or less.

If the component (C): an unsaturated compound is a polymer, component (C) can be produced by polymerizing a predetermined monomer.

Examples of the above-described monomer include, although are not especially limited to, conjugated dienes that generally has a hydrocarbon having 4 to about 12 carbon atoms, such as 1,3-butadiene, isoprene, 2,3-dimethylbutadiene, 1,3-pentadiene, 2-methyl-1,3-pentadiene, 1,3-hexadiene, 4,5-diethyl-1,3-octadiene, and 3-butyl-1,3-octadiene, monoterpene, vinyl aromatic compounds, norbornadiene, cyclopentadiene, cyclohexadiene, 2,3-dihydrodicyclopentadiene, acetylenes and the like.

These monomers may be used alone or two or more kinds may be copolymerized.

From the perspectives of the feed properties after storage of the catalyst composition for hydrogenation according to the present embodiment, and of little yellowing the polymer in the olefin compound hydrogenated using the catalyst composition for hydrogenation according to the present embodiment, a preferred range is specified for the unsaturated group content of unsaturated compound (C).

Namely, from the perspective of a high activity of hydrogenation and feed properties, it is preferred that the unsaturated group content of (C) is 2 mol or more based on 1 mol of (C). From the perspective of a high activity of hydrogenation, suppression of yellowing the polymer, 5 mol or less is preferred. A range of 2 mol or more to 4 mol or less is more preferred, and 3 mol is even more preferred.

The unsaturated group content of component (C) can be measured using NMR.

In addition, from the perspectives of the activity of hydrogenation and feed properties after storage of the catalyst composition for hydrogenation according to the present embodiment, it is that the mass ratio of component (C) to component (A) ((C)/(A)) is 0.1 or more. From the perspectives of the activity of hydrogenation, storage stability relating to feed properties, economic efficiency, and suppression of yellowing the polymer formed of the hydrogenated olefin compound of the catalyst composition for hydrogenation according to the present embodiment, the mass ratio is 4.0 or less.

It is preferred that the mass ratio of ((C)/(A)) of component (C) to component (A) is in the range of 0.5 to 3.0, and more preferred in the range of 1.0 to 2.5.

Still further, from the perspective of the feed properties after storage of the catalyst composition for hydrogenation according to the present embodiment, it is preferred that the molar ratio of the unsaturated group content of unsaturated compound (C) to the above-described a titanocene compound (A) (the unsaturated group content of (C)/(A)) is 0.1 or more. From the perspectives of the storage stability relating to feed properties and economic efficiency, suppression of yellowing the polymer, and a high activity of hydrogenation of the catalyst composition for hydrogenation according to the present embodiment, 25 or less is preferred.

It is more preferred that that the unsaturated group content of (C) is in the range of 0.6 to 20, and even more preferred in the range of 1.0 to 10.

As above-described, by setting the molecular weight of the unsaturated compound (C) of 400 or less, the catalyst composition for hydrogenation according to the present embodiment having high feed properties after storage is obtained. By setting the mass ratio of component (C) to component (A) ((C)/(A)) to 0.1 to 4.0, the catalyst composition for hydrogenation having a high activity of hydrogenation, feed properties after storage, and suppression effect of yellowing the polymer of the hydrogenated olefinic compound is obtained. Further, by setting the molar ratio of the unsaturated group content of (C) to component (A) to the above-described range, the amount of hydrogenating other than the olefinic unsaturated double bonds which is the target to be hydrogenated of the polymer can be reduced, and the catalyst composition having a high activity of hydrogenation can be obtained.

<Component (D): A Polar Compound>

Component (D): a polar compound (in the present specification, sometimes referred to simply as component (D) or (D)) is a compound having N, O, or S. Examples thereof include, but are not limited to, alcohol compounds, ether compounds, thioether compounds, ketone compounds, sulfoxide compounds, carboxylic acid compounds, carboxylate compounds, aldehyde compounds, lactam compounds, lactone compounds, amine compounds, amide compounds, nitrile compounds, epoxy oxime compounds, and oxime compounds.

Specific examples of these polar compounds are listed below.

Examples of the above-described alcohol compounds include, but are not limited to, monohydric alcohols, such as methyl alcohol, ethyl alcohol, propyl alcohol, n-butyl alcohol, sec-butyl alcohol, isobutyl alcohol, tert-butyl alcohol, n-amyl alcohol, iso-amyl alcohol, hexyl alcohol and isomers thereof, heptyl alcohol and isomers thereof, octyl alcohol and isomers thereof, caprylic alcohol, nonyl alcohol and isomers thereof, decyl alcohol and isomers thereof, benzyl alcohol, phenol, cresol, and 2,6-di-tert-butyl-p-cresol, and glycols (dihydric alcohols), such as ethylene glycol, propylene glycol, butanediol, pentyl glycol, hexyl glycol, heptyl glycol, and isomers thereof. Further, the alcohol compound may be a trihydric alcohol such as glycerin, or an alcohol compound having another functional group in one molecule, such as ethanolamine and glycidyl alcohol.

Examples of the above-described ether compounds include, but are not limited to, dimethyl ether, diethyl ether, di-n-propyl ether, diisopropyl ether, di-n-butyl ether, di-sec-butyl ether, diphenyl ether, methyl ethyl ether, ethyl butyl ether, butyl vinyl ether, anisole, ethyl phenyl ether, ethylene glycol dimethyl ether, ethylene glycol diethyl ether, ethylene glycol dibutyl ether, diethylene glycol dimethyl ether, diethylene glycol diethyl ether, furan, tetrahydrofuran, α-methoxy tetrahydrofuran, pyran, tetrahydropyran, dioxane and the like.

Further, the compound may be a compound having another functional group in a molecule, such as a tetrahydrofuran carboxylic acid.

Examples of the above-described thioether compounds include, but are not limited to, dimethyl sulfide, diethyl sulfide, di-n-butyl sulfide, di-sec-butyl sulfide, di-tert-butyl sulfide, diphenyl sulfide, methyl ethyl sulfide, ethyl butyl sulfide, thioanisole, ethyl phenyl sulfide, thiophene, tetrahydrothiophene and the like.

Examples of the above-described ketone compounds include, but are not limited to, acetone, diethyl ketone, di-n-propyl ketone, diisopropyl ketone, di-n-butyl ketone, di-sec-butyl ketone, di-tert-butyl ketone, benzophenone, methyl ethyl ketone, acetophenone, benzyl phenyl ketone, propiophenone, cyclopentanone, cyclohexanone, diacetyl, acetyl acetone, benzoyl acetone and the like.

Examples of the above-described sulfoxide compounds include, but are not limited to, dimethyl sulfoxide, diethyl sulfoxide, tetramethylene sulfoxide, pentamethylene sulfoxide, diphenyl sulfoxide, dibenzyl sulfoxide, p-tolyl sulfoxide and the like.

Examples of the above-described carboxylic acid compounds include, but are not limited to, monobasic acids, such as formic acid, acetic acid, propionic acid, butyric acid, caproic acid, lauric acid, palmitic acid, stearic acid, cyclohexyl propionic acid, cyclohexyl caproic acid, benzoic acid, phenylacetic acid, o-toluic acid, m-toluic acid, p-toluic acid, acrylic acid, and methacrylic acid, dibasic acids, such as oxalic acid, maleic acid, malonic acid, fumaric acid, succinic acid, adipic acid, pimelic acid, suberic acid, sebacic acid, itaconic acid, phthalic acid, isophthalic acid, terephthalic acid, naphthalic acid, and diphenic acid, as well as trimellitic acid/pyromellitic acid and derivatives thereof. Further, for example, the carboxylic acid compound may be a compound having another functional group in one molecule, such as hydroxy benzoic acid.

Examples of the above-described carboxylate include, but are not limited to, an ester of a monobasic acid, such as formic acid, acetic acid, propionic acid, butyric acid, caproic acid, lauric acid, palmitic acid, stearic acid, cyclohexyl propionic acid, cyclohexyl caproic acid, benzoic acid, phenylacetic acid, o-toluic acid, m-toluic acid, p-toluic acid, acrylic acid, and methacrylic acid, or a dibasic acid, such as oxalic acid, maleic acid, malonic acid, fumaric acid, succinic acid, adipic acid, pimelic acid, suberic acid, sebacic acid, itaconic acid, phthalic acid, isophthalic acid, terephthalic acid, naphthalic acid, and diphenic acid, with an alcohol, such as methyl alcohol, ethyl alcohol, propyl alcohol, n-butyl alcohol, sec-butyl alcohol, isobutyl alcohol, tert-butyl alcohol, n-amyl alcohol, iso-amyl alcohol, hexyl alcohol and isomers thereof, heptyl alcohol and isomers thereof, octyl alcohol and isomers thereof, caprylic alcohol, nonyl alcohol and isomers thereof, decyl alcohol and isomers thereof, benzyl alcohol, phenol, cresol, and glycidyl alcohol, a β-keto ester such as methyl acetoacetate or ethyl acetoacetate, and the like.

Examples of the above-described lactone compounds include, but are not limited to, β-propiolactone, δ-valerolactone, ε-caprolactone, and the lactone compounds corresponding to the following acids.

Namely, examples of the above-described acids include 2-methyl-3-hydroxypropionic acid, 3-hydroxynonane or 3-hydroxypelargonic acid, 2-dodecyl-3-hydroxypropionic acid, 2-cyclopentyl-3-hydroxypropionic acid, 2-n-butyl-3-cyclohexyl-3-hydroxypropionic acid, 2-phenyl-3-hydroxytridecanoic acid, 2-(2-ethylcyclopentyl)-3-hydroxypropionic acid, 2-methyl phenyl-3-hydroxypropionic acid, 3-benzyl-3-hydroxypropionic acid, 2,2-dimethyl-3-hydroxypropionic acid, 2-methyl-5-hydroxyvaleric acid, 3-cyclohexyl-5-hydroxyvaleric acid, 4-phenyl-5-hydroxyvaleric acid, 2-heptyl-4-cyclopentyl-5-hydroxyvaleric acid, 3-(2-cyclohexyl ethyl)-5-hydroxyvaleric acid, 2-(2-phenyl ethyl)-4-(4-cyclohexyl benzyl)-5-hydroxyvaleric acid, benzyl-5-hydroxyvaleric acid, 3-ethyl-5-isopropyl-6-hydroxycaproic acid, 2-cyclopentyl-4-hexyl-6-hydroxycaproic acid, 2-cyclopentyl-4-hexyl-6-hydroxycaproic acid, 3-phenyl-6-hydroxycaproic acid, 3-(3,5-diethyl-cyclohexyl)-5-ethyl-6-hydroxycaproic acid, 4-(3-phenyl-propyl)-6-hydroxycaproic acid, 2-benzyl-5-isobutyl-6-hydroxycaproic acid, 7-phenyl-6-hydroxyl-octoenoic acid, 2,2-di(1-cyclohexenyl)-5-hydroxy-5-heptenoic acid, 2,2-dipropenyl-5-hydroxy-5-heptenoic acid, 2,2-dimethyl-4-propenyl-3-hydroxy-3,5-heptadienoic acid and the like.

Examples of the above-described amine compounds include, but are not limited to, methylamine, ethylamine, isopropylamine, n-butylamine, sec-butylamine, tert-butylamine, n-amylamine, sec-amylamine, tert-amylamine, n-hexylamine, n-heptylamine, aniline, benzylamine, o-anisidine, m-anisidine, p-anisidine, α-naphthylamine, dimethylamine, diethylamine, di-n-propylamine, diisopropylamine, di-n-butylamine, di-sec-butylamine, diisobutylamine, di-tert-butylamine, di-n-amylamine, diisoamylamine, dibenzylamine, N-methylamine, N-ethylamine, N-ethyl-o-toluidine, N-ethyl-m-toluidine, N-ethyl-p-toluidine, triethylamine, tri-n-propylamine, tri-n-butylamine, tri-n-amylamine, triisoamylamine, tri-n-hexylamine, tribenzylamine, triphenyl methylamine, N,N-dimethyl benzylamine, N,N-dimethylamine, N,N-diethylamine, N,N-diethyl-o-toluidine, N,N-diethyl-m-toluidine, N,N-diethyl-p-toluidine, N,N-dimethyl-α-naphthylamine, N,N,N',N'-tetramethyl ethylene diamine, N,N,N',N'-tetraethyl ethylene diamine, pyrrolidine, piperidine, N-methylpyrrolidine, N-methylpiperidine, pyridine, piperazine, 2-acetylpyridine, N-benzylpiperazine, quinoline, morpholine and the like.

The above-described amide compound is a compound having at least one —C(=O)—N< or —C(=S)—N< bond in the molecule. Examples of this amide compound include, but are not limited to, N,N-dimethylformamide, N-dimethylacetamide, N-methylpyrrolidone, acetamide, propionamide, benzamide, acetanilide, benzanilide, N-methylacetanilide, N,N-dimethylthioformamide, N,N-dimethyl-N, N'-(p-dimethylamino)benzamide, N-ethylene-N-methyl-8-quiniline carboxyamide, N,N-dimethyl nicotinamide, N,N-dimethyl metaacrylamide, N-methylphthalimide, N-phenylphthalimide, N-acetyl-ε-caprolactam, N,N,N',N'-tetramethylphthalamide, 10-acetylphenoxazine, 3,7-bis(dimethylamino)-10-benzoylphenothiazine, 10-acetylphenothiazine, 3,7-bis)dimethylamino)-10-benzoylphenothiazine, N-ethyl-N-methyl-8-quinoline carboxyamide and the like. Further examples include straight-chain urea compounds, such as N,N'-dimethyl urea, N,N'-diethyl urea, N,N'-dimethyl ethylene urea, N,N,N',N'-tetramethyl urea, N,N-dimethyl-N', N'-diethyl urea, and N,N-dimethyl-N',N'-diphenyl urea.

Examples of the above-described epoxy compounds include, but are not limited to, 1,3-butadiene monoxide, 1,3-butadiene oxide, 1,2-butylene oxide, 2,3-butylene oxide, cyclohexene oxide, 1,2-epoxycyclododecane, 1,2-epoxydecane, 1,2-epoxyeicosane, 1,2-epoxyheptane, 1,2-epoxyhexadecane, 1,2-epoxyhexadecane, 1,2-epoxyoctadecane, 1,2-epoxyoctane, ethylene glycol diglycidyl ether, 1,2-epoxytetradecane, hexamethylene oxide, isobutylene oxide, 1,7-octadiene epoxide, 2-phenyl propylene oxide, propylene oxide, trans-stilbene oxide, styrene oxide, epoxylated 1,2-polybutadiene, epoxylated inseed oil, glycidyl methyl ether, glycidyl n-butyl ether, glycidyl allyl ether, glycidyl methacrylate, glycidyl acrylate and the like.

Examples of the above-described oxime compounds include, but are not limited to, acetoxime, methyl ethyl ketone oxime, diethyl ketone oxime, acetophenone oxime, benzophenone oxime, benzyl phenyl ketone oxime, cyclopentanone oxime, cyclohexanone oxime, benzaldehyde oxime and the like.

The above-described component (D): a polar compound can be used alone as one kind, or in combination of two kinds or more.

It is preferred that the polar compound is an amine compound or an ether compound. From the perspective of high activity of hydrogenation and high feed properties of the catalyst composition for hydrogenation, an amine compound is more preferred.

<Amount of Use of Component (D): Polar Compound>

From the perspectives of the activity of hydrogenation and storage stability relating to feed properties of the catalyst composition for hydrogenation according to the present embodiment, it is that the mass ratio of the above-described component (D) to the above-described component (A) ((D)/(A)) is 0.01 or more, and from the perspectives of the activity of hydrogenation, storage stability relating to feed properties, and economic efficiency of the catalyst composition for hydrogenation according to the present embodiment, 1.99 or less is preferred.

It is preferred that the mass ratio of the above-described component (D) to the above-described component (A) ((D)/(A)) is in a range of 0.015 to 0.500, and more preferred in a range of 0.020 to 0.300.

[Method for Producing Catalyst Composition for Hydrogenation]

The catalyst composition for hydrogenation according to the present embodiment can be produced by mixing the above-described component (A), component (B), component (C), and component (D), and optionally using a predetermined solvent.

In the method for producing the catalyst composition for hydrogenation according to the present embodiment, from the perspectives of high activity of hydrogenation, high feed properties, and colorlessness, it is preferred to lastly add component (B) in the coexistent of component (A), component (C), and component (D) to prepare the above-described component (A), component (B), component (C), and component (D). At this point, the order in which the above-described component (A), component (C), and component (D) are added may be freely selected, and is not especially limited.

The catalyst composition for hydrogenation may be introduced into a reaction system after preparing in advance in a catalyst tank separately to the reaction system of the target to be hydrogenated, or the components of the catalyst composition for hydrogenation may be individually introduced into the reaction system.

Since the catalyst composition for hydrogenation according to the present embodiment has a low viscosity, good feed properties, and excellent storage stability, this catalyst composition for hydrogenation is suited to a method in which the catalyst composition for hydrogenation is first prepared in a separate catalyst tank and then introduced into the reaction system of hydrogenation. The catalyst composition for hydrogenation is especially suited to a hydrogenation method in which the target to be hydrogenated and the catalyst composition for hydrogenation prepared in advance are continuously supplied (continuous hydrogenation).

If the target to be hydrogenated is a conjugated diene polymer or a copolymer formed of a conjugated diene and a vinyl aromatic hydrocarbon, and this polymer or copolymer is obtained by living anionic polymerization in which an organic alkali metal or an organic alkali earth metal is used as the initiator, when introducing the components of the catalyst composition for hydrogenation to the reaction system, a part or all of the active ends of the polymer or copolymer can also be used as component (B) above.

Further, after the polymerization of the target polymer or copolymer to be hydrogenated, a part or all of the active ends may be deactivated with a polymerization deactivator.

It is preferred that an alcohol or a ketone compound is used in excess as the polymerization deactivator. In the case of individually introducing the component of the catalyst composition for hydrogenation to the reaction system, if an excessive amount of deactivator is present in the reaction system, this excess amount may also be considered as component (D) or as a part of component (D). In such a case, the above-described mass ratio of component (D) to component (A) ((D)/(A)) is calculated by considering the excess amount of deactivator as component (D).

The atmosphere in which the catalyst composition for hydrogenation according to the present embodiment is prepared may be an inert gas atmosphere or a hydrogen atmosphere.

It is preferred that the preparing temperature and the storage temperature are in the range of −50° C. to 50° C., and more preferred are in the range of −20° C. to 30° C.

Although the time taken for preparation depends on the preparing temperature, the time is, under conditions of 25° C., a few seconds to 60 days, and the preferred time is 1 minute to 20 days.

When producing the catalyst composition for hydrogenation according to the present embodiment in advance in a catalyst tank separately to the reaction system for the target to be hydrogenated, it is preferred that component (A), component (B), component (C), and component (D) constituting the catalyst composition for hydrogenation according to the present embodiment are used as a solution dissolved in an inert organic solvent, because such a method facilitates handling.

The inert organic solvent that does not react with any of the participants in the hydrogenation reaction is used. The solvent is preferably the same as the solvent used in the hydrogenation reaction.

When producing the catalyst composition for hydrogenation according to the present embodiment in advance in a catalyst tank separately to the reaction system of the target to be hydrogenated, the produced catalyst composition for hydrogenation needs to be transferred to the reactor of hydrogenation (hydrogenation tank) in which the target to be hydrogenated is stored. It is preferred that transferring is under a hydrogen atmosphere.

Preferably, the temperature during the transferring is −30° C. to 100° C., and more preferably, the catalyst composition for hydrogenation is added just before the hydrogenation reaction at −10° C. to 50° C.

It is preferred that the mixing ratio of the respective components for exhibiting a high activity and selectivity of hydrogenation is, based on a ratio of the number of moles of the metal of component (B) and the number of moles of the metal (Ti) of component (A) (hereinafter, "Metal (B)/Metal (A) molar ratio"), in the range of about 20 or less.

Although it can be quantitatively hydrogenated based on thermal reduction even when the Metal (B)/Metal (A) molar ratio=0, i.e., when Metal (B) is not present, since this requires a higher temperature, a longer time, and a greater catalyst amount, it is preferred that Metal (B) is present.

By setting the Metal (B)/Metal (A) molar ratio to 20 or less, excessive use of the high-cost catalyst component (B), which is not involved in substantive improvement in activity, can be prevented, economic efficiency is excellent, and unnecessary side reactions can be prevented.

It is most preferred to select the mixing ratio of component (A) to component (B) so that the Metal (B)/Metal (A) molar ratio is in the range of 0.5 to 10, since the activity of hydrogenation of the catalyst composition for hydrogenation improves.

When the target to be hydrogenated is a living polymer obtained by living anionic polymerization, since the living ends act as a reductant, when hydrogenating a polymer having living active ends, to achieve the above-described optimum Metal (B)/Metal (A) molar ratio, it is preferred to deactivate the living active ends with various compounds having an active hydrogen or a halogen.

Examples of this compound having an active hydrogen include water, alcohols, such as methanol, ethanol, n-propanol, n-butanol, sec-butanol, t-butanol, 1-pentanol, 2-pentanol, 3-pentanol, 1-hexanol, 2-hexanol, 3-hexanol, 1-heptanol, 2-heptanol, 3-heptanol, 4-heptanol, octanol, nonanol, decanol, undecanol, lauryl alcohol, allyl alcohol, cyclohexanol, cyclopentanol, and benzyl alcohol, phenols, such as phenol, o-cresol, m-cresol, p-cresol, p-allyl phenol, 2,6-di-t-butyl-p-cresol, xylenol, dihydroanthraquinone, dihydroxycoumarin, 1-hydroxyanthraquinone, m-hydroxybenzyl alcohol, resorcinol, and leucoaurine, and the like.

Further, examples of the acid include organic carboxylic acids, such as acetic acid, propionic acid, butyric acid, isobutyric acid, pentanoic acid, hexanoic acid, heptanoic acid, decalin acid, myristic acid, stearic acid, behenic acid, and benzoic acid.

In addition, examples of the compound having a halogen include benzyl chloride, trimethylsilyl chloride (bromide), t-butylsilyl chloride (bromide), methyl chloride (bromide), ethyl chloride (bromide), propyl chloride (bromide), n-butyl chloride (bromide) and the like.

These can be used alone as one kind, or in combination of two kinds or more.

[Method for Hydrogenation Using Catalyst Composition for Hydrogenation]

In the present embodiment, it is hydrogenated by bringing an olefinic unsaturated double bond-containing compound into contact with hydrogen in the presence of the above-described catalyst composition for hydrogenation according to the present embodiment.

The catalyst composition for hydrogenation according to the present embodiment can be used in the step of hydrogenating all of the olefinic unsaturated double bond-containing compounds.

Examples of the olefinic unsaturated double bond-containing compound include, but are not limited to, aliphatic olefins of isomers and the like of ethylene, propylene, butene, pentene, hexene, heptene, octene and the like; alicyclic olefins, such as cyclopentene, methylcyclopentene, cyclopentadiene, cyclohexene, methylcyclohexene, and cyclohexadiene; monomers, such as styrene, butadiene, and isoprene; unsaturated fatty acids and derivatives thereof, unsaturated liquid oligomers and the like, low-molecular-weight polymers containing at least one olefinic unsaturated double bond in the molecule and the like.

Further, the catalyst composition for hydrogenation according to the present embodiment can also be applied in selective hydrogenation of the olefinic unsaturated double bonds of a conjugated diene polymer or of a copolymer formed of a conjugated diene and an olefinic monomer.

Here, selective hydrogenation referred to herein means selectively hydrogenating the olefinic unsaturated double bonds of a conjugated diene polymer or of a conjugated diene moiety of a copolymer formed of a conjugated diene and an olefinic monomer. Specifically, selective hydrogenation means that, when a vinyl aromatic compound, for example, a vinyl aromatic hydrocarbon, is used as the olefinic monomer, the carbon-carbon double bond of the aromatic ring is essentially not hydrogenated.

A production of the selective hydrogenation of the olefinic unsaturated double bonds of a conjugated diene polymer or of a copolymer formed of a conjugated diene and an olefinic monomer is industrially useful for elastic bodies and thermoplastic elastic bodies.

Examples of the conjugated diene used in producing the conjugated diene polymer, which is the above-described target to be hydrogenated, generally include conjugated dienes having 4 to about 12 carbon atoms.

Examples thereof include, but are not limited to, 1,3-butadiene, isoprene, 2,3-dimethyl-1,3-butadiene, 1,3-pentadiene, 2-methyl-1,3-pentadiene, 1,3-hexadiene, 4,5-diethyl-1,3-octadiene, 3-butyl-1,3-octadiene and the like.

From the perspective of obtaining an elastic body that can be advantageously developed industrially and that has excellent physical properties, 1,3-butadiene and isoprene are preferred.

Although the microstructure of the butadiene moiety has 1,2-bonds and 1,4-bonds (cis+trans), the catalyst composition for hydrogenation according to the present embodiment can quantitatively hydrogenate either of these.

Further, although the isoprene moiety has 1,2-bond and 3,4-bond side chains and an olefinic unsaturated bond on a 1,4-bond (cis+trans) main chain, the catalyst composition for hydrogenation obtained based on the method for production according to the present embodiment can quantitatively hydrogenate either of these.

The structure and hydrogenation ratio of the compound hydrogenated by the catalyst composition for hydrogenation according to the present embodiment can be identified and measured using 1H-NMR.

Based on the method for hydrogenation using the catalyst composition for hydrogenation according to the present embodiment, the 1,2-bonds and the 1,4-bonds of the butadiene moiety and the 1,2-bond and 3,4-bond side chains of the isoprene moiety can especially be selectively hydrogenated.

It is preferred that the main component of the conjugated diene polymer hydrogenated by the catalyst composition for hydrogenation has, when 1,3-butadiene is selected, especially to exhibit elastomer elasticity in a low temperature to room temperature, a 1,2-bond content as the microstructure of the butadiene unit moiety of the target to be hydrogenated of 8% or more. More preferred is 20% or more, and an especially preferred range is 30 to 80%.

For the same reason, when isoprene is selected as the main component of the conjugated diene polymer hydrogenated by the catalyst composition for hydrogenation, it is preferred that the 1,4-bond content as the microstructure of the isoprene unit is 50% or more, and more preferred is 75% or more.

To sufficiently exhibit the effect of selectively hydrogenating only the unsaturated double bond of the conjugated diene unit, and to obtain an industrially useful, and high-value elastic body or thermoplastic elastic body, it is especially preferred that the target to be hydrogenated is a copolymer formed of a conjugated diene and a vinyl aromatic hydrocarbon. Examples of the vinyl aromatic hydrocarbon that can be copolymerized with at least one kind of conjugated diene include styrene, tert-butylstyrene, α-methylstyrene, p-methylstyrene, divinylbenzene, 1,1-diphenylethylene, N,N-dimethyl-p-aminoethylstyrene, N,N-diethyl-p-aminoethylstyrene and the like. Styrene and/or α-methylstyrene is especially preferred.

As examples of specific copolymers, butadiene/styrene copolymers, isoprene/styrene copolymers, butadiene/isoprene/styrene copolymers and the like are preferred since they are capable of providing a hydrogenated copolymer with high industrial value. These copolymers may be in any form, such as random, block, tapered block copolymers and the like.

If the below-described preferred hydrogenating conditions are selected using the catalyst composition for hydrogenation according to the present embodiment, hydrogenating the carbon-carbon double bond (aromatic ring) of the vinyl aromatic hydrocarbon unit in this copolymer essentially does not occur.

It is preferred that the hydrogenation reaction using the catalyst composition for hydrogenation according to the present embodiment is carried out by bringing compound having an olefinic unsaturated double bond into contact with hydrogen in a solution in which an inert organic solvent is dissolved.

The "inert organic solvent" referred to herein means a solvent that does not react with any of the participants in the hydrogenation reaction. Examples of such an inert organic solvent include, aliphatic hydrocarbons, such as n-pentane, n-hexane, n-heptane, and n-octane, alicyclic hydrocarbons, such as cyclohexane, cycloheptane, and cycloheptane, ethers, such as diethyl ether and tetrahydrofuran and the like, which are used alone or as a mixture. Further, aromatic hydrocarbons, such as benzene, toluene, xylene, and ethylbenzene, may also be used only on condition that the aromatic double bond is not hydrogenated under the conditions of selected hydrogenation conditions.

The hydrogenation reaction is generally carried out by holding the above-described target solution to be hydrogenated at a predetermined temperature under a hydrogen or inert atmosphere, adding the catalyst composition for hydrogenation under stirring or without stirring, and then introducing hydrogen gas to increase the pressure to a predetermined level. The term inert atmosphere means an atmosphere, such as nitrogen, helium, neon, and argon, that does not react with any of the participants in the hydrogenation reaction. Air and oxygen are not preferred, because they can lead to deactivation of the catalyst composition for hydrogenation by oxidizing the catalyst component.

Since the catalyst composition for hydrogenation according to the present embodiment has a low viscosity, good feed properties, and excellent storage stability, the catalyst composition for hydrogenation is suited to a method for hydrogenation in which the target to be hydrogenated and the catalyst composition for hydrogenation are continuously supplied to the reactor of hydrogenation (continuous hydrogenation).

It is preferred that the added amount of the catalyst composition for hydrogenation in the step of hydrogenation is in the range of, based on the molar amount of component (A), 0.001 to 20 mmol based on 100 g of the target to be hydrogenated.

If the added amount is within this range, A very high selective hydrogenation can be realized, because the olefinic unsaturated double bonds of the target to be hydrogenated can be preferentially hydrogenated, and hydrogenating the double bond of the aromatic ring in the copolymer essentially does not occur.

Although a hydrogenation reaction is possible even when the catalyst composition for hydrogenation is added in an amount of more than 20 mmol per 100 g of the target to be hydrogenated based on the molar amount of component (A), using more of the catalyst that is not economically efficient, and leads to disadvantages such as the deashing and removal of the catalyst after the hydrogenation reaction becoming more complex.

Further, the preferred added amount of the catalyst composition for hydrogenation for quantitatively adding the unsaturated double bond of the conjugated diene unit of the polymer under the selected conditions is, based on the molar amount of component (A), 0.01 to 5 mmol per 100 g of the target to be hydrogenated.

It is more preferred that the hydrogenation reaction proceeds under stirring, as this reaction enables the introduced hydrogen to be sufficiently and quickly brought into contact with the target to be hydrogenated.

It is preferred that the hydrogenation reaction proceeds in a temperature range of 0 to 200° C.

The reaction at 0° C. or more enables the reaction to proceed at a sufficient rate of hydrogenation, and prevents the need for a large amount of catalyst. Further, the reaction at 200° C. or less allows side reactions, a degradation reaction, gellation, and associated reactions to be prevented, as well as allowing the deactivation of the catalyst composition for hydrogenation and deterioration of activity of hydrogenation to be prevented.

A more preferred temperature range is 20 to 180° C.

A preferred pressure of the hydrogen used in the hydrogenation reaction is 1 to 100 kgf/cm$^2$.

If the hydrogen pressure is less than 1 kgf/cm$^2$, the rate of hydrogenation may decrease, and a sufficient hydrogenation ratio may not likely be obtained. If the hydrogen pressure is more than 100 kgf/cm$^2$, the hydrogenation reaction is almost complete simultaneously with the increase in pressure, and unnecessary side reactions and gellation may likely occur.

A more preferred hydrogen pressure of hydrogenation is 2 to 30 kgf/cm$^2$. However, it is preferred to select the optimum hydrogen pressure in correlation with the added amount of the catalyst composition for hydrogenation and the like. In practice, it is preferred that the hydrogenation reaction proceeds in a hydrogen pressure selected on the high side as the amount of the above-described catalyst composition for hydrogenation decreases.

Further, the reaction time of hydrogenation is usually from a few seconds to 50 hours.

The reaction time and pressure of hydrogenation are appropriately selected within the above-described ranges based on the desired hydrogenation ratio.

Based on the above-described step of hydrogenation, an arbitrary hydrogenation ratio is obtained for the olefinic unsaturated double bonds of the olefinic compound, and the olefinic unsaturated double bonds in the conjugated diene polymer and in the copolymer formed of a conjugated diene and a vinyl aromatic hydrocarbon based on the intended objective.

After the hydrogenation reaction using the catalyst composition for hydrogenation according to the present embodiment, the hydrogenated product can be easily separate from the solution in which the hydrogenated product is contained by chemical means or physical means, such as distillation and precipitation.

Especially, if the target to be hydrogenated is a polymer, a residue of the catalyst composition for hydrogenation can be removed as necessary from the polymer solution on which the hydrogenation reaction proceeds, and the hydrogenated polymer separated from the solution.

Examples of the separation method include a method involving adding a polar solvent, such as acetone or alcohol, which is a poor solvent for the hydrogenated polymer, to the reacted solution of hydrogenation, which causes the hydrogenated polymer to precipitate for collection, a method involving charging the reacted solution into hot water under stirring, then distilling and collecting the hydrogenated polymer together with the solvent for collection, a method involving directly distilling off the solvent by heating the reaction solution, and collecting the hydrogenated polymer.

Examples

The present invention will now be described in more detail with reference to specific examples and comparative examples. However, the present invention is not limited to the following examples.

The constituent components of the catalyst composition for hydrogenation used in the examples and comparative examples are shown below.

[Component (A)]

<(A-1): Synthesis of bis(η(5)-cyclopentadienyl)titanium di-(p-tolyl)>

A 1-L, three-necked flask equipped with a stirrer, a dropping funnel, and a reflux condenser was charged with 200 mL of anhydrous ether.

The apparatus was dried with dry helium, a small piece of lithium wire (17.4 g (2.5 mol)) was cut and dropped into the flask, and a small amount of a solution of 300 mL of ether and 171 g (1 mol) of p-bromotoluene was added dropwise to the flask at room temperature. Then, the whole amount of the solution of p-bromotoluene in ether was gradually added.

After the reaction has finished, the reacted solution was filtered under a helium atmosphere to obtain a colorless, transparent p-tolyl lithium solution.

A 2-L, three-necked flask purges with dry helium and equipped with a stirrer and a dropping funnel was charged with 99.6 g (0.4 mol) of bis(η(5)-cyclopentadienyl)titanium dichloride and 500 mL of anhydrous ether.

The above-synthesized solution of p-tolyl lithium in ether was added dropwise for about 2 hours at room temperature under stirring.

The reaction mixture was filtered in air, and the non-dissolved portion was washed with dichloromethane. Then, the filtrate and the washing solution were combined, and the solvent was removed under a reduced pressure.

The resultant residue was dissolved in a small amount of dichloromethane. Then, petroleum ether was added to recrystallize.

An operation of filtering the obtained crystals and then again concentrating the filtrate was repeatedly carried out to obtain bis(η(5)-dichloropentadienyl)titanium di(p-tolyl).

The yield was 87%.

The obtained crystals were orange-yellow, had a needle shape, exhibited good solubility in toluene and cyclohexane, had a melting point of 145° C., and had elemental analysis values of C, 80.0, H, 6.7, and Ti, 13.3.

<(A-2): Synthesis of bis(η(5)-cyclopentadienyl)titanium di(phenyl)>

Phenyl lithium was obtained by being synthesized in the same manner as in the above (A-1), except that 157 g of bromobenzene (1 mol) was used instead of the p-bromotoluene used in the above-described (A-1). Using this phenyl lithium, bis(η(5)-cyclopentadienyl)titanium diphenyl was obtained based on the same steps as in the above-described (A-1). The obtained amount was 120 g (yield of 90%).

The obtained crystals were orange-yellow, had a needle shape, exhibited fairly good solubility in toluene and cyclohexane, had a melting point of 147° C., and had elemental analysis values of C, 79.5, H, 6.1, and Ti, 14.4.

<(A-3): Synthesis of bis(η(5)-cyclopentadienyl)titanium di(3,4-xylyl)>

Bis(η(5)-cyclopentadienyl)titanium di(3,4-xylyl) was obtained by being synthesized in the same manner as in the above (A-1), except that 4-bromo-o-xylene (1 mol) was used instead of the p-bromotoluene used in the above-described (A-1). The yield was 83%.

The obtained crystals were orange-yellow, had a needle shape, exhibited good solubility in toluene and cyclohexane, had a melting point of 155° C., and had elemental analysis values of C, 80.6, H, 7.2, and Ti, 12.2.

<(A-4): Bis(η(5)-1,3-dimethylcyclopentadienyl)titanium dichloride>

A product obtained by recrystallizing a reagent manufactured by Nihon Fine Chemical Co., Ltd., in dichloromethane was used.

[Component (B)]
(B-1): Triethylaluminum

A hexane solution (manufactured by Tosoh Corporation/Akzo Corporation) was used as it is.
(B-2): sec-Butyllithium A hexane solution (manufactured by Kanto Chemical Co., Inc.) was filtered under an inert atmosphere, and the resultant yellow, transparent portion was used.

[Component (C)]

The following commercially available reagent grade regents were used for the below (C-1) to (C-4).
(C-1): Myrcene (molecular weight 136, number of unsaturated groups based on 1 mole of (C-1): 3 moles)
(C-2): Isoprene (molecular weight 68, number of unsaturated groups based on 1 mole of (C-2): 2 moles)
(C-3): Octene (molecular weight 112, number of unsaturated groups based on 1 mole of (C-3): 1 mole)
(C-4): 1,7-Octadiene (molecular weight 110, number of unsaturated groups based on 1 mole of (C-4): 2 moles)
(C-5): Polyisoprene (number average molecular weight measured by GPC: 3,100, number of unsaturated groups based on 1 mole of (C-5): 46 moles)

[Component (D)]
Commercially available reagent grade regents were all used.
(D-1): Tetrahydrofuran
(D-1): Ethyl acetate
(D-1): N,N,N',N'-Tetramethylethylenediamine Preparation of Catalyst Composition for Hydrogenation (Examples 1 to 15) and (Comparative Examples 1 to 5)

Component (A), component (B), component (C), and component (D) were added in the ratios shown in the following Table 1 to produce a cyclohexane solution having the final concentration of 5% by mass.

The components were added in an order so that component (B) was lastly added in the coexistent of component (A), component (C), and component (D).

[Polymer]
(Polymerization of Styrene-Butadiene-Styrene Block Copolymer)

A 7 L autoclave was charged with 4,000 g of cyclohexane, 150 g of styrene monomer, 1.10 g of n-butyl lithium, and 25 g of tetrahydrofuran. The resultant mixture was polymerized for 3 hours at 60° C. under stirring. Then, 700 g of 1,3-butadiene monomer was added, and the mixture was polymerized for 3 hours at 60° C.

Lastly, 150 g of styrene monomer was added, and the mixture was polymerized for 3 hours at 60° C.

The active ends were deactivated with water, and the resultant product was vacuum-dried for 12 hours at 60° C.

The obtained styrene-butadiene-styrene block copolymer was completely a block copolymer, having a bound styrene content of 30% by mass, a 1,2-vinyl bond content of the butadiene unit of 45 mol %, and a weight average molecular weight measured by GPC (in terms of polystyrene) of about 60,000.

The 1,2-vinyl bond content was measured using NMR.
[Evaluation Methods]
<Hydrogenation Ratio>

A reaction of hydrogenating a polymer was as shown in Production Examples 1 to 15 and Comparative Production Examples 1 to 5, which were production examples of the below-described hydrogenated polymer, and the hydrogenation ratio of the obtained hydrogenated polymer was measured using the NMR described below.

After the catalyst compositions for hydrogenation of Examples 1 to 15 and Comparative Examples 1 to 5 were prepared, a case in which the catalyst composition for hydrogenation was used immediately after (initial) being prepared and a case in which the catalyst composition for hydrogenation was used after storing for 30 days at 30° C. after preparation were both evaluated.

For both cases, a higher hydrogenation ratio was better. Cases in which the hydrogenation ratio was 99.5% or more were evaluated with a "⊚", 99.0% or more to less than 99.5% evaluated with a "○", 97.0% or more to less than 99.0% evaluated with a "△", and less than 97.0% evaluated with a "x".
(NMR: Measurement Method of 1,2-Vinyl Bond Content and Hydrogenation Ratio)

The 1,2-vinyl bond content and the hydrogenation ratio of the unsaturated groups in the conjugated diene was measured under the following conditions by nuclear magnetic resonance spectroscopy (NMR).

After the hydrogenation reaction, the hydrogenated polymers were collected by precipitating with a large amount of methanol, then extracted with acetone, vacuum dried, and subjected to 1H-NMR measurement.
Measurement equipment: JNM-LA400 (manufactured by JEOL)
Solvent: Deuterated chloroform
Measurement sample: Extracted before and after hydrogenating the polymer
Sample concentration: 50 mg/mL
Observation frequency: 400 MHz
Chemical shift standard: TMS (tetramethylsilane)
Pulse delay: 2.904 seconds
Number of scans: 64 times
Pulse width: 45°
Measurement temperature: 26° C.
<Feed Properties>
After the catalyst compositions for hydrogenation of Examples 1 to 15 and Comparative Examples 1 to 7, the feed properties were evaluated after storing for 30 days at 30° C. by flowing 1 liter of the catalyst compositions for hydrogenation through a 1 liter separating funnel (SPC 29, manufactured by Sibata Scientific Technology).
Cases in which there was no clogging and the catalyst composition for hydrogenation flowed continuously were good and evaluated with a "○", cases in which the catalyst composition for hydrogenation flowed intermittently evaluated with a "Δ", and cases in which there was clogging were evaluated with a "x".
<Suppression of Yellowing Hydrogenated Polymer>
A hydrogenation reaction proceeded using a catalyst composition for hydrogenation stored for 30 days after preparation in a 30° C. environment under the same conditions as in the above-described "Hydrogenation Ratio". Namely, the hydrogenation reaction proceeded as shown in the below-described Production Examples 1 to 15 and Comparative Production Examples 1 to 5, which were hydrogenated polymer production examples. Then, methanol water was added, and next, based on 100 parts by mass of the hydrogenated polymer produced as described above, 0.3 parts by mass of octadecyl-3-(3,5-di-t-butyl-4-hydroxyphenyl)propionate was added as a stabilizer, and then the solvent was dried. The obtained hydrogenated polymer was visually observed for yellowing when press-molded for 10 minutes at 200° C.
No coloration was better, so cases in which there was no coloration were evaluated with a "○", and cases in which there was coloration were evaluated with a "x".

Production Examples 1 to 15 and Comparative Production Examples 1 to 5

A 1,000 mL pressure-resistant autoclave with the inside replaced with hydrogen was charged with a polymer: styrene-butadiene-styrene block copolymer produced as described above as an 80 g purified and dried cyclohexane solution (solution concentration 10% by mass).
Catalyst compositions for hydrogenation of Production Examples 1 to 15 and Comparative Production Examples 1 to 5 were charged into a pressure-resistant autoclave so that the Ti content was 150 ppm based on the above-described polymer, and subjected to a hydrogen pressure of 5 kgf/cm$^2$.
A hydrogenation reaction proceeded for 20 minutes at 100° C. under stirring.
Hydrogenated polymers produced as described above using the catalyst compositions for hydrogenation of Production Examples 1 to 15 and Comparative Production Examples 1 to 5 were taken as the polymers of Production Examples 1 to 15 and Comparative Production Examples 1 to 5, respectively.
The following Table 1 shows the hydrogenation ratio of the hydrogenated polymers of Production Examples 1 to 15 and Comparative Production Examples 1 to 5, and evaluation of the feed properties of the catalyst compositions for hydrogenation of Examples 1 to 15 and Comparative Examples 1 to 5 and suppression of yellowing the hydrogenated polymers of Production Examples 1 to 15 and Comparative Production Examples 1 to 5, respectively.

TABLE 1

The constituent components of the catalyst composition for hydrogenation are shown in Table 1.

| | | Catalyst Composition for Hydrogenation | | | | | | | Evaluation Results | | | |
| --- | --- | --- | --- | --- | --- | --- | --- | --- | --- | --- | --- | --- |
| | | (A) | | (B) | | (C) | | (D) | | Hydrogenation Ratio of Polymer | Feed Properties of Catalyst Composition for Hydrogenation | Suppression of Yellowing Hydrogenated Polymer |
| | | Type | (mmol) | Type | (mmol) | Type | Mass Ratio Based on (A) (—) | Type | Mass Ratio Based on (A) (—) | Initial / After 30 Days | After 30 Days | |
| Example | 1 | A-1 | 0.015 | B-1 | 0.0375 | C-1 | 2 | D-1 | 0.3 | ○ / ○ | ○ | ○ |
| | 2 | A-2 | 0.015 | B-1 | 0.0375 | C-1 | 2 | D-1 | 0.3 | ○ / ○ | ○ | ○ |
| | 3 | A-3 | 0.015 | B-1 | 0.0375 | C-1 | 2 | D-1 | 0.3 | ○ / ○ | ○ | ○ |
| | 4 | A-4 | 0.015 | B-1 | 0.0375 | C-1 | 2 | D-1 | 0.3 | ○ / ○ | ○ | ○ |
| | 5 | A-1 | 0.015 | B-1 | 0.0375 | C-1 | 2 | D-1 | 0.015 | ○ / ○ | Δ | ○ |
| | 6 | A-1 | 0.015 | B-1 | 0.0375 | C-1 | 2 | D-1 | 0.5 | ○ / ○ | Δ | ○ |
| | 7 | A-1 | 0.015 | B-1 | 0.0375 | C-1 | 2 | D-1 | 0.9 | ○ / Δ | Δ | ○ |
| | 8 | A-1 | 0.015 | B-1 | 0.0375 | C-1 | 4 | D-1 | 0.3 | ○ / Δ | Δ | ○ |
| | 9 | A-1 | 0.015 | B-2 | 0.0375 | C-1 | 2 | D-1 | 0.3 | ⊙ / ⊙ | ○ | ○ |
| | 10 | A-1 | 0.015 | B-1 | 0.0375 | C-2 | 2 | D-1 | 0.3 | ○ / Δ | ○ | ○ |
| | 11 | A-1 | 0.015 | B-2 | 0.0375 | C-2 | 2 | D-1 | 0.3 | ⊙ / ○ | ○ | ○ |
| | 12 | A-1 | 0.015 | B-1 | 0.0375 | C-3 | 2 | D-1 | 0.3 | ○ / Δ | Δ | ○ |
| | 13 | A-1 | 0.015 | B-1 | 0.0375 | C-4 | 2 | D-1 | 0.3 | ○ / Δ | ○ | ○ |

TABLE 1-continued

The constituent components of the catalyst composition for hydrogenation are shown in Table 1.

| | | Catalyst Composition for Hydrogenation | | | | | | Evaluation Results | | | |
|---|---|---|---|---|---|---|---|---|---|---|---|
| | | (A) | | (B) | | (C) | | (D) | | Hydrogenation Ratio of Polymer | Feed Properties of Catalyst Composition for Hydrogenation | Suppression of Yellowing |
| | | Type | (mmol) | Type | (mmol) | Type | Mass Ratio Based on (A) (−) | Type | Mass Ratio Based on (A) (−) | Initial | After 30 Days | After 30 Days | Hydrogenated Polymer |
| | 14 | A-1 | 0.015 | B-1 | 0.0375 | C-1 | 2 | D-2 | 0.3 | ○ | △ | ○ | ○ |
| | 15 | A-1 | 0.015 | B-1 | 0.0375 | C-1 | 2 | D-3 | 0.3 | ◉ | ○ | ○ | ○ |
| Comparative Example | 1 | A-1 | 0.015 | B-1 | 0.0375 | — | — | — | — | △ | X | X | ○ |
| | 2 | A-1 | 0.015 | B-1 | 0.0375 | C-1 | 2 | — | — | △ | X | X | ○ |
| | 3 | A-1 | 0.015 | B-1 | 0.0375 | C-1 | 2 | D-1 | 1.5 | △ | △ | X | ○ |
| | 4 | A-1 | 0.015 | B-1 | 0.0375 | C-1 | 10 | — | — | △ | X | X | X |
| | 5 | A-4 | 0.015 | B-1 | 0.0375 | C-5 | 2 | D-1 | 0.3 | △ | X | X | X |

Component (A)
(A-1): bis (η (5)-cyclopentadienyl) titanium di (p-tolyl)
(A-2): bis (η (5)-cyclopentadienyl) titanium di (phenyl)
(A-3): bis (η (5)-cyclopentadienyl) titanium di (3,4-xylyl)
(A-4): bis (η (5)-1,3-dimethylcyclopentadienyl) titanium dichloride
Component (B)
(B-1): Triethylaluminum
(B-2): sec-Butyllithium
Component (C)
(C-1): Myrcene
(C-2): Isoprene
(C-3): Octene
(C-4): 1,7-Octadiene
(C-5): Polyisoprene
Component (D)
(D-1): Tetrahydrofuran
(D-1): Ethyl acetate
(D-1): N,N,N',N'-Tetramethylethylenediamine It was found that the catalyst compositions for hydrogenation of Examples 1 to 15, which include component (A), component (B), component (C), and component (D), and have a mass ratio of component (C) to component (A) ((C)/(A)) of 0.1 to 4.0 and a mass ratio of (D) to (A) ((D)/(A)) in the range of 0.01 to 1.00, can produce a hydrogenated olefin compound having a high activity of hydrogenation, good feed properties, excellent storage stability, and excellent non-coloration properties.

The present application is based on a Japanese patent application (Japanese Patent Application No. 2012-208283) filed with the Japan Patent Office on Sep. 21, 2012, and the entire contents thereof are incorporated herein by reference.

INDUSTRIAL APPLICABILITY

The catalyst composition for hydrogenation according to the present invention has industrial applicability as a catalyst composition for hydrogenation to be used in a step of hydrogenation for producing a hydrogenated polymer compound that can be used as a polypropylene and polyethylene improver.

The invention claimed is:
1. A catalyst composition, comprising compounds (A), (B), (C), and (D) shown below,
wherein a mass ratio of the compound (C) to the compound (A) (the compound (C)/the compound (A)) is in a range of 2.0 to 4.0,
a mass ratio of the compound (D) to the compound (A) (the compound (D)/the compound (A)) is in a range of 0.01 to 1.00,
the compound (A) comprises a titanocene compound represented by following general formula (1),

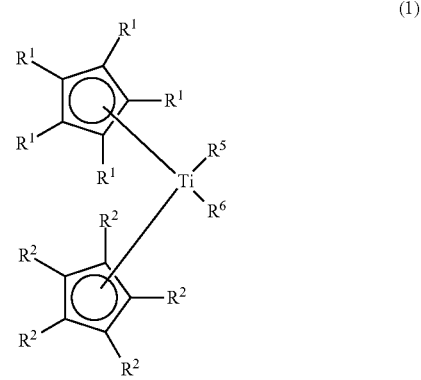

(wherein $R^5$ and $R^6$ represent a group selected from the group consisting of a hydrocarbon group having 1 to 8 carbon atoms, an aryloxy group having 1 to 8 carbon atoms, an alkoxy group having 1 to 8 carbon atoms, and a halogen group, $R^5$ and $R^6$ may be the same or different; and $R^1$ represents a group selected from the group consisting of hydrogen and a hydrocarbon group having 1 to 4 carbon atoms, $R^2$ represents a group selected from the group consisting of hydrogen and a hydrocarbon group having 1 to 4 carbon atoms, and $R^1$ and $R^2$ may be the same or different), the compound (B) is an organic compound comprising one or more elements selected from the group consisting of elements Li and Al, the compound (C) comprises a compound selected from the group consisting of unsaturated compounds that have a hydrocarbon having 4 to 12 carbon atoms, the compound (C) has a molecular weight of 400 or less, and the compound (D) comprises a polar compound selected from the group consisting of ether compounds, carboxylate compounds, and amine compounds, wherein the ether compounds are selected from the group consisting of dimethyl ether, diethyl ether, di-n-propyl ether, diisopropyl ether, di-n-butyl ether, di-sec-butyl ether, diphenyl ether, methyl ethyl ether, ethyl butyl ether, butyl vinyl ether, anisole, ethyl phenyl ether, ethylene glycol dimethyl ether, ethylene glycol diethyl ether, ethylene glycol dibutyl ether, diethylene glycol dimethyl ether, diethylene glycol diethyl ether, furan, tetrahydrofuran, a-methoxy tetrahydrofuran, pyran, tetrahydropyran, and dioxane; tetrahydrofuran carboxylic acid;

the carboxylate compounds are selected from the group consisting of methyl or ethyl esters of formic acid, acetic acid, propionic acid, butyric acid, caproic acid, lauric acid, palmitic acid, stearic acid, cyclohexyl propionic acid, cyclohexyl caproic acid, benzoic acid, phenylacetic acid, o-toluic acid, m-toluic acid, p-toluic acid, acrylic acid, methacrylic acid, oxalic acid, maleic acid, malonic acid, fumaric acid, succinic acid, adipic acid, pimelic acid, suberic acid, sebacic acid, itaconic acid, phthalic acid, isophthalic acid, terephthalic acid, naphthalic acid, and diphenic acid; and methyl acetoacetate or ethyl acetoacetate; and the amine compounds are selected from the group consisting of methylamine, ethylamine, isopropylamine, n-butylamine, sec-butylamine, tert-butylamine, n-amylamine, sec-amylamine, tert-amylamine, n-hexylamine, n-heptylamine, aniline, benzylamine, o-anisidine, m-anisidine, p-anisidine, α-naphthylamine, dimethylamine, diethylamine, di-n-propylamine, diisopropylamine, di-n-butylamine, di-sec-butylamine, diisobutylamine, di-tert-butylamine, di-n-amylamine, diisoamylamine, dibenzylamine, N-methylamine, N-ethylamine, N-ethyl-o-toluidine, N-ethyl-m-toluidine, N-ethyl-p-toluidine, triethylamine, tri-n-propylamine, tri-n-butylamine, tri-n-amylamine, triisoamylamine, tri-n-hexylamine, tribenzylamine, triphenyl methylamine, N,N-dimethyl benzylamine, N,N-dimethylamine, N,N-diethylamine, N,N-diethyl-o-toluidine, N,N-diethyl-m-toluidine, N,N-diethyl-p-toluidine, N,N-dimethyl-a-naphthylamine, N,N,N',N'-tetramethyl ethylene diamine, N,N,N',N'-tetraethyl ethylene diamine, pyrrolidine, piperidine, N-methylpyrrolidine, N-methylpiperidine, pyridine, piperazine, 2-acetylpyridine, N-benzylpiperazine, quinoline, and morpholine.

2. The catalyst composition according to claim 1, wherein the compound (C) has an unsaturated group content of 2 mol or more based on 1 mol of the compound (C).

3. The catalyst composition according to claim 1, wherein the compound (B) is an organic lithium compound.

4. A method of hydrogenating a compound, comprising bringing an olefinic unsaturated double bond-containing compound into contact with hydrogen in an inert organic solvent, in the presence of the catalyst composition according to claim 1.

5. The method according to claim 4, wherein the olefinic unsaturated double bond-containing compound is a conjugated diene polymer or a copolymer formed of a conjugated diene and a vinyl aromatic hydrocarbon.

6. The catalyst composition according to claim 2, wherein the compound (B) is an organic lithium compound.

7. The catalyst composition according to claim 1, wherein the compound (A) is selected from the group consisting of bis(η(5)-methylcyclopentadienyl)titanium dichloride, bis(η(5)-n-butylcyclopentadienyl)titanium dichloride, bis(η(5)-methylcyclopentadienyl)titanium diphenyl, bis(η(5)-n-butylcyclopentadienyl)titanium diphenyl, bis(η(5)-methylcyclopentadienyl)titanium di(p-tolyl) and bis(η(5)-n-butylcyclopentadienyl)titanium di(p-tolyl).

8. The catalyst composition according to claim 1, wherein the compound (A) is selected from the group consisting of bis(η(5)-cyclopentadienyl)titanium di(p-tolyl), bis(η(5)-cyclopentadienyl)titanium di(phenyl), bis(η(5)-cyclopentadienyl)titanium di(3,4-xylyl) and bis(η(5)-1,3-dimethylcyclopentadienyl)titanium dichloride.

9. The catalyst composition according to claim 1, wherein the compound (B) is triethylaluminum or sec-butyllithium.

10. The catalyst composition according to claim 1, wherein the compound (C) is selected from the group consisting of myrcene, isoprene, octene, 1,7-Octadiene and polyisoprene.

11. The catalyst composition according to claim 10, wherein the compound (C) has an unsaturated group content of 2 mol or more and 5 mol or less based on 1 mol of the compound (C).

12. The catalyst composition according to claim 10, wherein the compound (C) has an unsaturated group content of 2 mol or more and 4 mol or less based on 1 mol of the compound (C).

13. The catalyst composition according to claim 1, wherein the compound (D) is an amine compound or an ether compound.

14. The catalyst composition according to claim 1, wherein the compound (D) is tetrahydrofuran, ethyl acetate or N,N,N',N'-Tetramethylethylenediamine.

15. The method according to claim 4, wherein the olefinic unsaturated double bond-containing compound is styrene-butadiene-styrene block copolymer.

16. A method of hydrogenating a compound, comprising bringing an olefinic unsaturated double bond-containing compound into contact with hydrogen in an inert organic solvent, in the presence of the catalyst composition according to claim 2.

17. The method according to claim 16, wherein the olefinic unsaturated double bond-containing compound is a conjugated diene polymer or a copolymer formed of a conjugated diene and a vinyl aromatic hydrocarbon.

18. A method of hydrogenating a compound, comprising bringing an olefinic unsaturated double bond-containing compound into contact with hydrogen in an inert organic solvent, in the presence of the catalyst composition according to claim 3.

19. The method according to claim 18, wherein the olefinic unsaturated double bond-containing compound is a conjugated diene polymer or a copolymer formed of a conjugated diene and a vinyl aromatic hydrocarbon.

20. The method according to claim 1, wherein the compound (B) comprises a compound containing Al.

21. The method according to claim 1, wherein the compound (C) comprises a compound selected from the group consisting of 1,3-butadiene, isoprene, 2,3-dimethylbutadiene, 1,3-pentadiene, 2-methyl-1,3-pentadiene, 1,3-hexadiene, 4,5-diethyl-1,3-octadiene, and 3-butyl-1,3-octadiene.

22. The catalyst composition according to claim 1, wherein
  $R^1$ represents a group selected from the group consisting of hydrogen, methyl group, ethyl group, propyl group and butyl group, and
  $R^2$ represents a group selected from the group consisting of hydrogen, methyl group, ethyl group, propyl group and butyl group.

23. The catalyst composition according to claim 1, wherein
  $R^5$ and $R^6$ represent a group selected from the group consisting of methyl group, ethyl group, butyl group, hexyl group octyl group, phenyl group, tolyl group, xylyl group, ethyl phenyl group, hexyl phenyl group, benzyl fluoride group, methoxide group, ethoxide group, propoxide group, butoxide group, phenoxide group, chloride group, bromide group, and iodide group.

24. The catalyst composition according to claim 1, wherein the compound (C) comprises a hydrocarbon diene that has 4 to 12 carbon atoms or 2,3-dihydrocyclopentadiene.

25. The catalyst composition according to claim 1, wherein the compound (C) comprises monoterpene or 2,3-dihydrodicyclopentadiene.

* * * * *